(12) United States Patent
 Rakeman

(10) Patent No.: US 9,778,199 B2
(45) Date of Patent: Oct. 3, 2017

(54) CLASSIFICATION AND IDENTIFICATION OF SOLID PROPELLANT ROCKET MOTORS

(71) Applicant: Raytheon Company, Waltham, MA (US)

(72) Inventor: James W. Rakeman, Brea, CA (US)

(73) Assignee: Raytheon Command and Control Solutions LLC, Fullerton, CA (US)

( * ) Notice: Subject to any disclaimer, the term of this patent is extended or adjusted under 35 U.S.C. 154(b) by 1008 days.

(21) Appl. No.: 14/270,855

(22) Filed: May 6, 2014

(65) Prior Publication Data

US 2015/0323448 A1    Nov. 12, 2015

(51) Int. Cl.
| | |
|---|---|
| *G01N 21/27* | (2006.01) |
| *F02K 9/08* | (2006.01) |
| *G01S 13/58* | (2006.01) |
| *G01N 21/71* | (2006.01) |
| *G01J 3/433* | (2006.01) |
| *F41H 11/02* | (2006.01) |

(Continued)

(52) U.S. Cl.
CPC ............... *G01N 21/71* (2013.01); *F02K 9/08* (2013.01); *F41H 11/02* (2013.01); *G01J 3/433* (2013.01); *G01N 21/27* (2013.01); *G01S 13/58* (2013.01); *G01S 13/72* (2013.01); *G01S 13/86* (2013.01); *G01N 21/716* (2013.01); *G01N 2201/12* (2013.01)

(58) Field of Classification Search
CPC . F02K 9/08; F41H 11/02; G01J 3/433; G01N 21/27; G01N 21/71; G01S 13/58; G01S 13/72; G01S 13/862
See application file for complete search history.

(56) References Cited

U.S. PATENT DOCUMENTS 7,295,149 B1 *  11/2007  Wolf ...................... F41G 7/007
                                                               342/90

OTHER PUBLICATIONS

Culick et al. "Combustion Instabilities in Soup Propellant Rocket Motors," Notes for Two Lectures given as part of the Special Course Internal Aerodynamics in Solid Rocket Propulsion von Karman Institute May 27-31, 2002.*

(Continued)

*Primary Examiner* — Paul D Lee
*Assistant Examiner* — Mark Crohn
(74) *Attorney, Agent, or Firm* — Eric A. Gifford

(57) ABSTRACT

Pressure variations within a solid propellant rocket motor produce like variations in the optical radiance of the motor exhaust plume. The periodicity of the variation is related to the length L of the rocket motor or speed of sound in the rocket motor combustion chamber to length ratio a/L. The optical radiance is collected and converted to electrical signals that are sampled at or above the Nyquist rate. An array of single-pixel photo detectors is well suited to provide amplitude data at high sample rates. The sampled data from the one or more detectors is assembled to form a high fidelity time sequence. A window of sampled data is processed to form a signal frequency spectrum. The mode structure in the frequency spectrum is related to the rocket motor length or speed of sound in the rocket motor chamber to length ratio. The rocket motor length or speed of sound to length ratio is used alone or in combination with other information to either classify or identify the rocket motor.

18 Claims, 5 Drawing Sheets

(51) Int. Cl.
   *G01S 13/72*    (2006.01)
   *G01S 13/86*    (2006.01)

(56)                References Cited

OTHER PUBLICATIONS

R. L. Proffit et al., "Rocket Stability Monitoring by Temporal Radiometry," AIAA 5th Propulsion Joint Specialist Conference, U. S. Air Force Academy, Colorado, Jun. 9-13, 1969.*
China CZ-4, <https://blackboard.tudelft.nl/bbcswebdav/users/bzandbergen/LVC/ Launch%20Vehicle%20Catalogue/Fiches/CZ-4.pdf>(retrieved Jan. 31, 2017).*
Roh et al, "Numerical study of acoustic oscillations and combustion instabilities in solid propellant rocket," In: Proceedings of the 34th JANNAF Combustion Subcommittee Meeting, 1997, . CPIA publication. vol. 2. No. 662. Chemical Propulsion Information Agency, Laurel, MD, pp. 141-151. http://resolver.caltech.edu/.
Culick et al. "Combustion Instabilities in Solid Propellant Rocket Motors," Notes for Two Lectures given as part of the Special Course \Internal Aerodynamcis in Solid Rocket Propulsion von karman Institute May 27-31, 2002.

* cited by examiner

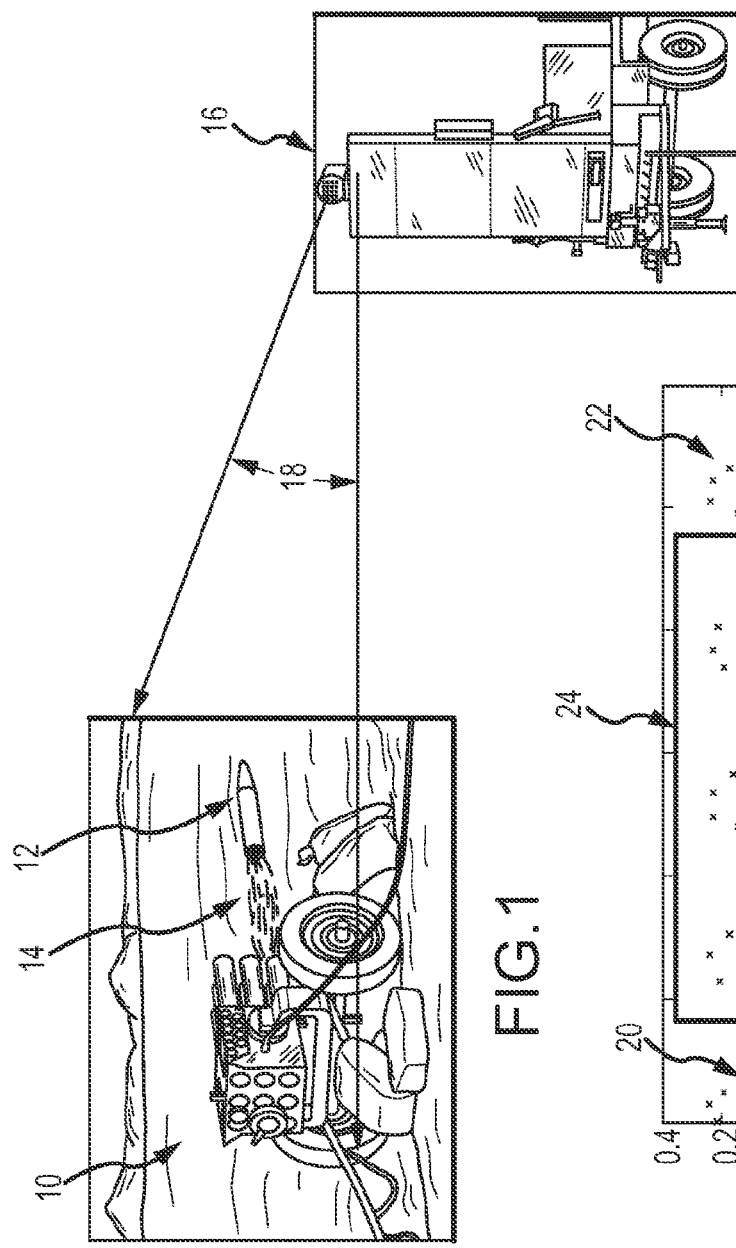
FIG.1
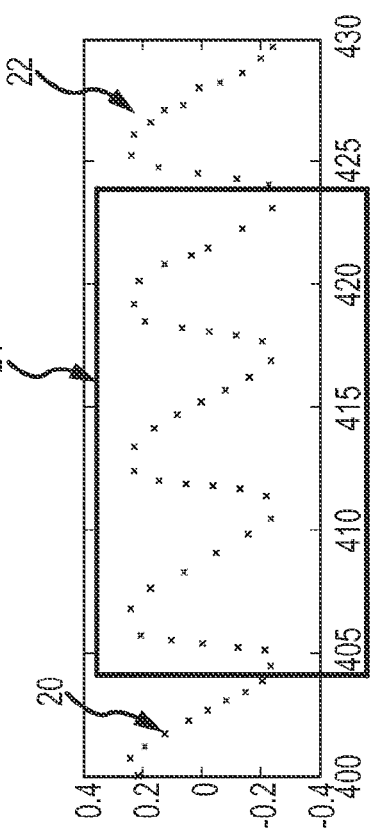
FIG.2
FIG.3

CLASSIFICATION AND IDENTIFICATION OF SOLID PROPELLANT ROCKET MOTORS

BACKGROUND OF THE INVENTION

Field of the Invention

This invention relates to the classification and identification of solid propellant rockets, and more particularly to the detection and processing of the optical radiance of the rocket motor exhaust plume to classify and identify rockets.

Description of the Related Art

Rocket motors or a "rocket" is a jet engine that uses only stored propellant mass for forming its high speed propulsive jet. Since they need no external material to form their jet, rocket motors can be used for spacecraft propulsion as well as terrestrial uses such as missiles or aircraft. Rocket motors produce thrust by expulsion of a high-speed fluid exhaust. This fluid is nearly always a gas which is created by high pressure combustion of solid or liquid propellants, consisting of fuel and oxidiser components, within a combustion chamber. The fluid exhaust is then passed through a supersonic propelling nozzle which uses heat energy of the gas to accelerate the exhaust to very high speed, and the reaction to this pushes the rocket in the opposite direction.

Real-time or near real-time classification and identification of rockets via remote sensing has applications both to forensic analysis for peacekeeping operations or to live battlefield conditions to aid in the determination of a firing point to direct counter-fire or an impact point to provide advance warning to friendly troops. "Classification" generally refers to placement of the rocket within a defined class such as short, mid or long range or light, medium or heavy. For example, light rockets may range in caliber from 80 to 122 mm, medium from 122 to 200 and heavy from 200 to 240. "Identification" generally refers to the determination of a particular rocket e.g. a 107 mm rocket.

Radar installations use radio waves to determine range, altitude, direction and speed of objects. Radar can be used to detect and track the flight of a rocket based on the reflected radio frequency energy off of the rocket body. The radar unit can model the ballistic trajectory of the rocket and extrapolate forward and backward to estimate the impact point and firing point, respectively. The radar unit may attempt to classify the rocket based on its ballistic trajectory. Classification accuracy is limited and latency is dictated by having to estimate the ballistic trajectory over some portion of the flight.

Optical sensing installations use pixelated imagers to detect passive optical radiance e.g. visible or IR bands, from the rocket to form an image of the rocket. The image provides spatial information as to the size, shape and features of the rocket that can be used to classify, or possibly identify the rocket. Over useful fields of view and ranges this requires a high resolution imager. In the IR band, high resolution imagers are typically expensive. In the visible band, high resolution imagers are readily available but are limited to use in the daylight.

SUMMARY OF THE INVENTION

The following is a summary of the invention in order to provide a basic understanding of some aspects of the invention. This summary is not intended to identify key or critical elements of the invention or to delineate the scope of the invention. Its sole purpose is to present some concepts of the invention in a simplified form as a prelude to the more detailed description and the defining claims that are presented later.

The present invention provides for classification and identification of solid propellant rockets.

This is accomplished by detecting and processing the optical radiance of the rocket exhaust plume to extract a rocket motor signature that is indicative of a particular class of rockets or particular rocket.

In an embodiment, the frequency of the dominant mode of the exhaust plume luminance provides the motor signature in the form of the length (L) or speed of sound (a) in the rocket motor combustion chamber to length ratio (a/L) of the motor that can be used alone, or in combination with other inputs, to classify or identify the rocket.

In an embodiment, the optical radiance of the rocket motor's exhaust plume is collected over a field of view, sensed and converted to an electrical signal that is sampled at or above the Nyquist rate. The sampled data is assembled into a high fidelity time sequence. A window of sampled data in the time sequence is processed to generate a signal frequency spectrum. The frequency of the dominant mode maps to the length L or to the ratio a/L of the velocity-of-sound in the rocket compression chamber to the length of the rocket motor. The motor length or sound velocity to length ratio can be used alone, or in combination with other inputs, to classify or identify the rocket.

In different embodiments, the optical radiance may be collected and sensed using a single detector such as a single pixel photo detector or a pixelated imager or an array of such detectors. In the latter case, the detectors are synchronized to a reference clock signal and the data is assembled e.g. concatenated or composited, to form the high fidelity sequence of sampled data. The detectors may be configured for a single spectral band such as visible, IR or UV or for multiple spectral bands.

In an embodiment, the motor length, sound velocity to length ratio or the classification or identification of the rocket may be provided to a radar unit to augment the unit's ballistic modeling to improve the forward and backward extrapolation to better, and more quickly, estimate the impact point or firing point.

These and other features and advantages of the invention will be apparent to those skilled in the art from the following detailed description of preferred embodiments, taken together with the accompanying drawings, in which:

BRIEF DESCRIPTION OF THE DRAWINGS

FIG. 1 is an illustration of a rocket launched from a portable rocket launcher;

FIG. 2 is an illustration of a flash detector and rocket classification unit configured to detect rocket launch and process the optical radiance of the rocket exhaust plume to classify and identify the rocket;

FIG. 3 is an example of a window of optical radiance data sampled at or above the Nyquist rate;

DETAILED DESCRIPTION OF THE INVENTION

Figure 4:
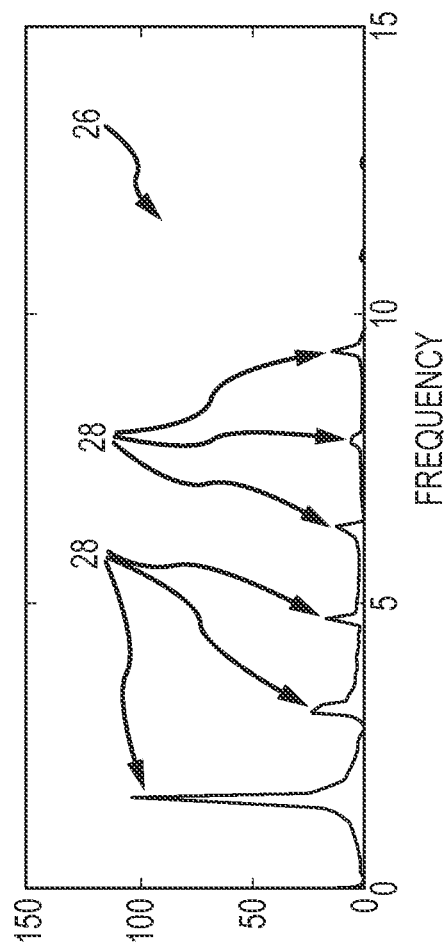
FIG. 4 is a plot of a frequency spectrum of the window of sampled data.
Figure 5:
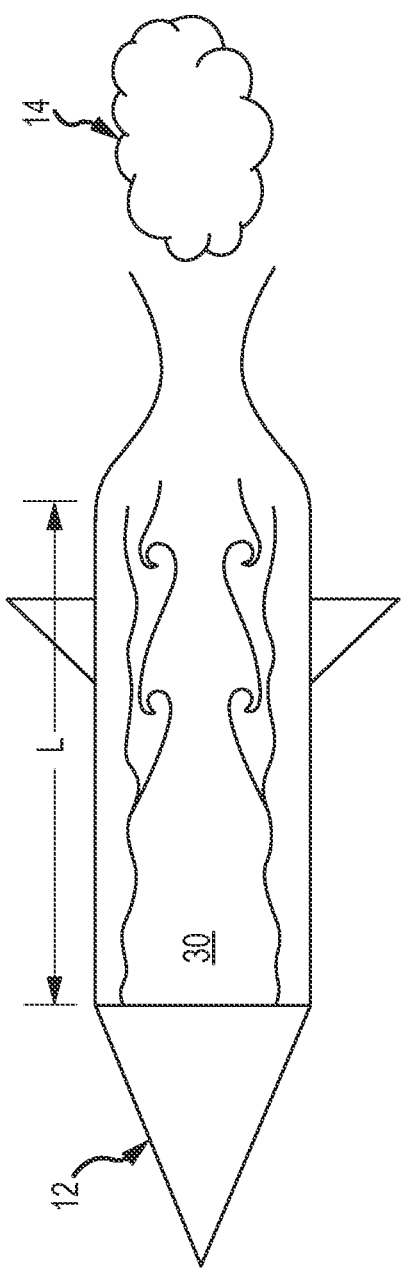
FIG. 5 is an illustration of an embodiment of a rocket having a rocket motor length L.

The present invention provides for classification and identification of solid propellant rockets. This is accomplished by detecting and processing the optical radiance of the rocket exhaust plume to extract a rocket motor signature that is indicative of a particular class of rockets or particular rocket. More particularly, the dominant frequency mode of the exhaust plume provides a motor signature in the form of the length of the motor L or the sound velocity to length ratio a/L that can be used alone, or in combination with other inputs, to classify or identify the rocket.

It has been known for some time that solid propellant rocket motors exhibit combustion instabilities resulting from acoustic waves within the combustion chamber. A body of research exists that has attempted to accurately characterize the source of the instabilities and predict their behavior. The literature has characterized the instabilities as periodic pressure variations within the rocket motor combustion chamber. This research is directed to gaining a better understanding of the thrust properties of solid propellant motors to inform a better design of solid rocket motors.

This research is presented in F. E. C. Culick, "Combustion Instabilities In Solid Propellant Rocket Motors" May 2002, which is hereby incorporated by reference. Relatively straightforward mathematical relationships have been developed that relate the pressure variations within the combustion chamber to rocket motor design characteristics, including motor length. As shown in FIG. 1.6 the frequency response of the pressure within the combustion chamber for a solid rocket propellant exhibits periodic bulk and $1^{st}$, $2^{nd}$ . . . order modes. As given by equation 2.61, these longitudinal modes have frequencies $f_a = l/*\pi*(a/L)$ where a is the speed of sound in the chamber, L is the length of the rocket motor and l=1, 2, 3 . . . identifies the mode.

The velocity of speed of sound inside the chamber is strongly dependent on chamber pressure and may vary from rocket to rocket. If the variation is significant, the variation contributes to the uniquely identifiable features of the rocket and the identification metric is a/L. If, for the class of rockets to be identified, the variation in chamber pressure is small, then L can be uniquely calculated and forms the unique identification metric.

Variations in rocket motor pressure (and the associated vortex shedding) can be discerned in the radiance of the rocket exhaust plume. Variations have been observed at both visible and infrared wavelengths. If these optical variations are related to the pressure variations predicted, than a means of inferring rocket motor length L or velocity of sound to length ratio a/L can be devised relying on the periodicity of the variations. The motor length or sound velocity to length ratio can then be used to classify and perhaps identify the rocket without requiring an image of the rocket itself. To improve classification or identification, the motor length or sound ratio may be fused with other inputs.

Referring now to FIGS. 1 through 5, in an embodiment, an enemy rocket launcher 10 launches a rocket 12 at a friendly position. Expulsion of hot high-pressure gas from rocket 12 produces an exhaust plume 14 from launch through flight until the rocket motor burns out. Exhaust plume 14 produces an optical radiance in both the visible and IR bands. One or more forward deployed flash detection and rocket classification units 16 passively collect optical radiance in one or more spectral bands over a field-of-view (FOV) 18 that encompasses the launch and initial flight of the rocket and its exhaust plume. For most spectral bands, the unit requires a direct line-of-sight of the exhaust plume. However, for SWIR the unit may collect radiance scattered off the atmosphere.

Flash detection and classification unit 16 detects the optical radiance of the rocket's exhaust plume in the one or more spectral bands and converts the optical radiance to an electrical signal. A function of unit 16 is to detect the "flash" associated with a rocket launch event in order to provide a warning to friendly troops. The unit may also process the signal to estimate time of launch, burn time and bearing to the rocket. For purposes of classification and identification, the flash and detected event trigger the collection and assembly of a window of high fidelity sampled data. In most systems, classification and identification will be provided in addition to the launch warning although for purposes of classification/identification issuance of the warning is not required.

The electrical signal is sampled at or above the Nyquist rate of twice the highest measurable frequency component of amplitude modulation of the optical radiance to generate sampled data that is stored. By sampling at or above the Nyquist rate aliasing of the light amplitude modulation is avoided in subsequent spectral analysis. The shortest motor length or highest sound velocity to length ratio suitably determines the Nyquist rate. Synchronized sampled data 20 from one or more detectors is assembled to form a high fidelity time sequence 22 for the optical radiance of the exhaust plume. The assembly removes any spatial information from the raw sample data. For a single one-pixel photo detector the output is simply sampled to assemble the sequence of sampled data. For an array of photo detectors, the different streams of sampled data are either concatenated or composited to form sequence 22.

Assuming normalization of the photo detector data, sampled data may be concatenated by selecting the largest amplitude response at each time sample to form the high fidelity sequence. Sampled data may be composited by identifying the photo detector with the largest amplitude response at each time sample, summing the amplitude responses in a given region of interest around that detector and concatenating the summed values. The region of interest could be limited to just the photo detectors adjacent the detector with the maximum amplitude response at a given time sample or could be the entire array or any region in between. For an imager or array of imagers, the largest pixel selected from a sequential series of correlated images could be concatenated to form the optical amplitude signal.

A window 24 of the assembled sampled data 20 is processed (e.g. Fourier or Cepstral) to generate a signal frequency spectrum 26 for the optical radiance of the exhaust plume. The duration of window 24 may be fixed to provide a desired frequency resolution or allowed to vary to capture the exhaust plume from launch through motor burn out. The signal frequency spectrum 26 for the optical radiance of the exhaust plume has a similar mode structure 28 to the frequency response of the pressure within the combustion chamber as reported by Culick.

The frequency f of the modes l=1, 2, 3, . . . is given by $f_{a^n} = l/*\pi*(a/L)$ where a is the speed of sound in the chamber and L is the length of the rocket motor (i.e. the length of combustion chamber 30). The length of the rocket motor L or the ratio (a/L) of the speed of sound in the chamber can be determined from the frequency of any of modes, assuming the mode number is known, or the difference between mode frequencies. Typically, the dominant mode, 1, and its frequency will be extracted and used to compute motor length L or to (a/L). The dominant mode may be identified by thresholding the amplitudes of the frequency response, ordering the modes by amplitude and selecting the largest one.

Unit 16 may use the length L or ratio (a/L) of the rocket motor to classify or identify the rocket. Unit 16 may be configured to use only the length L or ratio (a/L) to classify or identify the rocket. Alternately, unit 16 may be configured to fuse other inputs, if available, to improve the classification or identification of the rockets. Other inputs may include, but are not limited to, ballistic information (velocity, drag acceleration) or radar cross-section from a radar unit, other sensor data such as acoustic or other optical data or a priori knowledge of the classes or particular rockets available in a specific scenario.

The ability to classify or identify the rocket may depend on various factors. Does the application require specific identification of the rocket or is classification adequate? What is the frequency resolution of the mode structure, hence the accuracy of the motor length estimate? Accuracy may be affected by how clean the optical radiance signal is and the length of the window. The longer the window, the finer the frequency resolution of the signal frequency spectrum. This can also be affected by the granularity in length of particular rockets or classes of rockets or by variations in the velocity of sound in the rocket motor chamber. Are other inputs available, and to what extent do those inputs further discriminate individual rocket motors?

Figure 6:
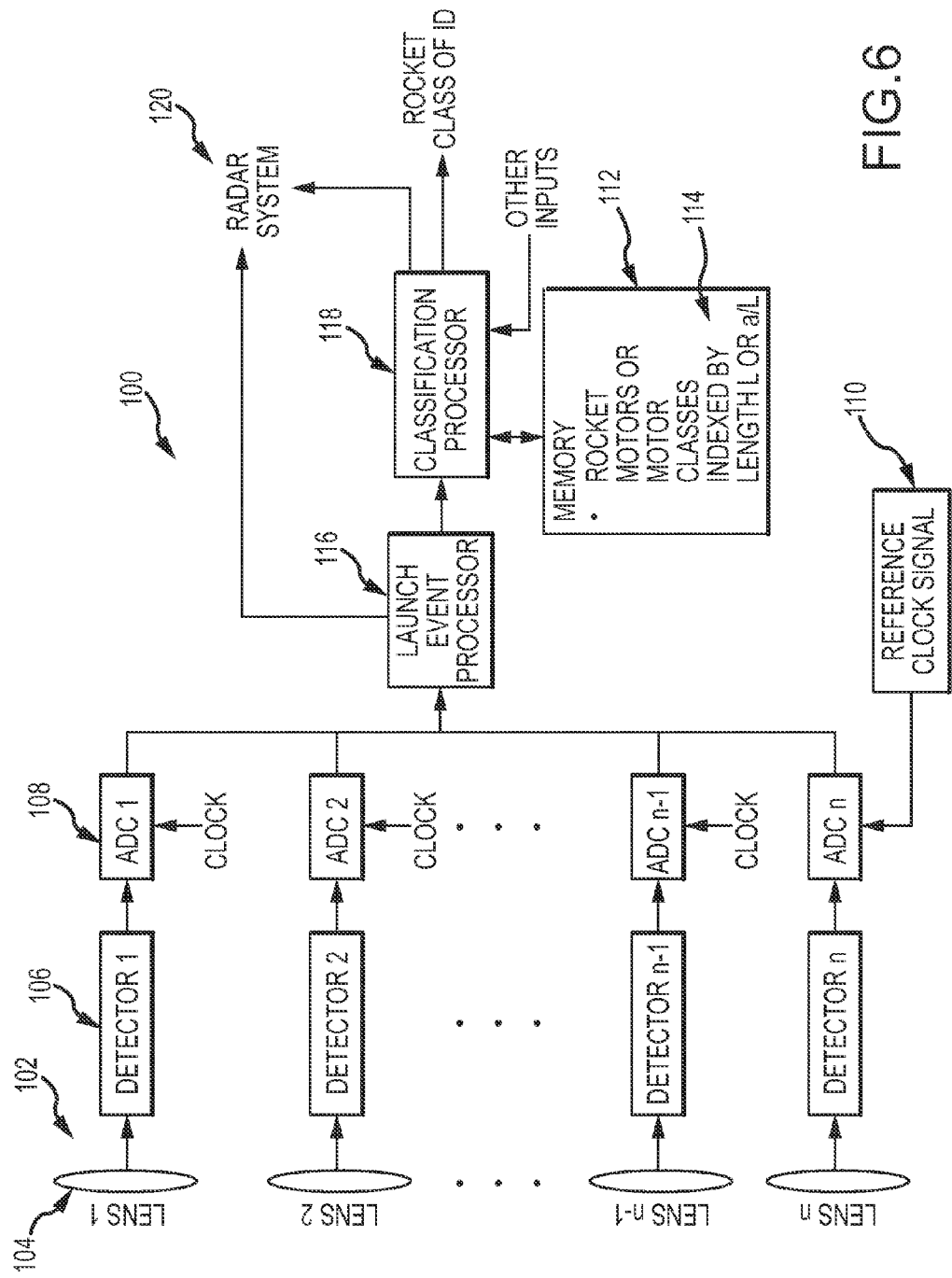
FIG. 6 is a block diagram of an embodiment of flash detector and rocket classification unit employing an array of single pixel photo detectors.
Figure 7:
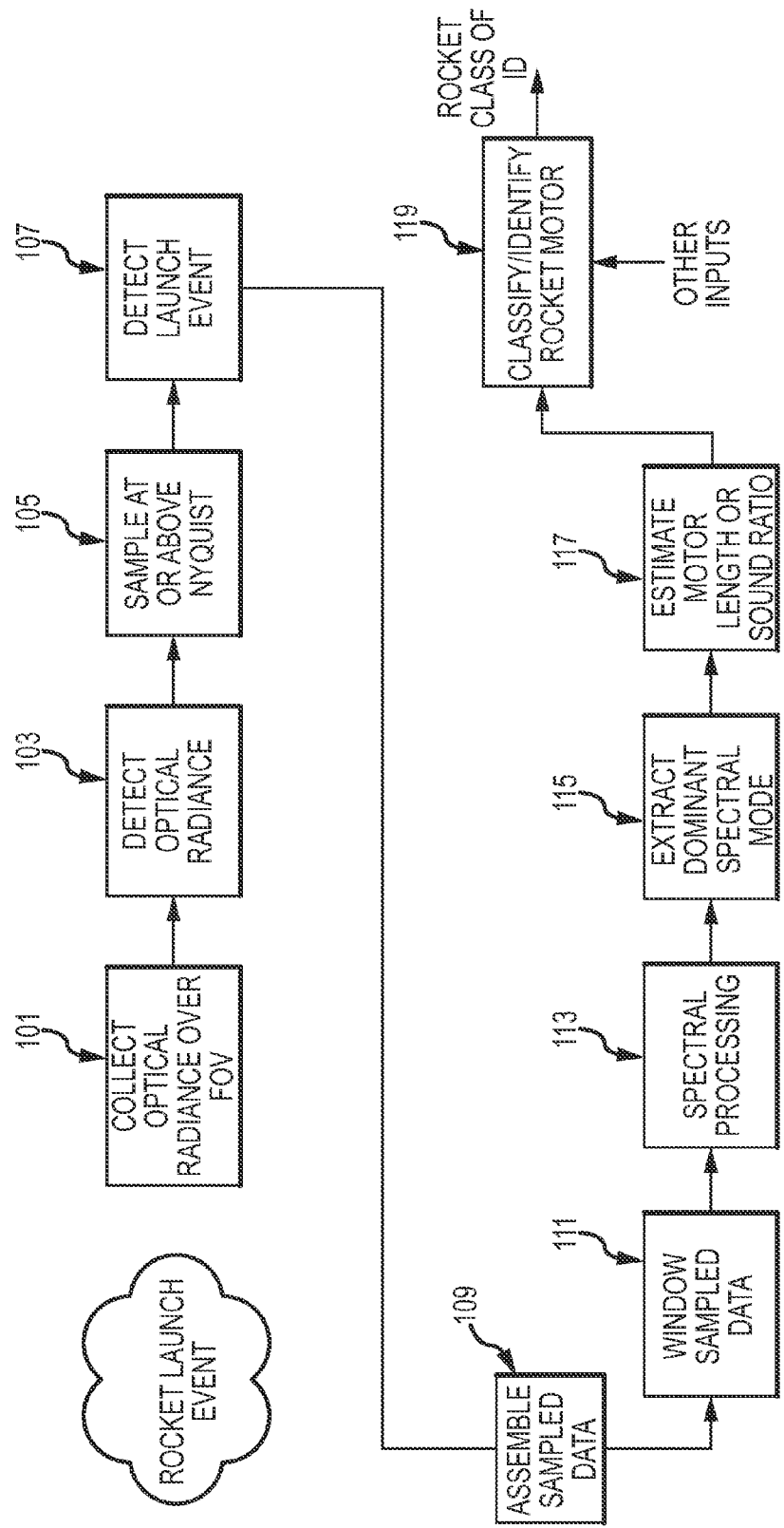
FIG. 7 is a flow diagram for the embodiment of FIG. 6.

Referring now to FIGS. 6 and 7, an embodiment of a flash detection and classification unit 100 comprises an optical array 102 of collection optics 104 configured to collect optical radiance (step 101) in a spectral band over an array of overlapping fields-of-view (FOV) that encompass a rocket launch event and initial flight of the rocket and its exhaust plume. An array of one pixel photo detectors 106 sensitive to the spectral band is arranged to detect optical radiance from the overlapping FOV and convert the optical radiance to analog electrical signals (step 103). An exemplary photo detector is Cal Sensors Model Series SCD-15.

An array of analog-to-digital converters 108 is configured to sample the array of analog electrical signals at or above the Nyquist rate of twice the highest measurable frequency component of amplitude modulation of the optical radiance (step 105) to generate a plurality of sequences of sampled data that are synchronized to a reference clock signal 110. A sample rate of 5-10 KHz would be at or above the Nyquist rate for rocket motor (a/L) ratios of less than about 1600.

A library 112 of rocket classes or individual rockets indexed by rocket motor length L or (a/L) is stored in computer memory 114. For example, rocket classes such as light, medium and heavy may each have an associated nominal motor length or (a/L) or a range of motor lengths or ratios. Individual rocket motors may be indexed with a specific length or speed of sound to length ratio.

One or more computer processors may be configured functionally as a launch event processor 116 and a classification processor 118. Launch event processor 116 is suitably configured to perform the standard tasks associated with a flash detection unit of processing the sampled data to detect a rocket launch event (step 107). The event processor 116 may also estimate the rise and fall times and envelope characteristics of the launch event, rocket burn time, bearing angle to the rocket and other characteristics.

To detect launch events, the sampled photo-detector data is accumulated and stored. The amplitude of the data is tested against a threshold and, if high enough, a launch event is declared. The data associated with that detection is analyzed to determine if it has the characteristics of a valid rocket motor or is a false alarm. If it is valid, the leading edge is estimated (launch event time) and the duration of the event determined (burn time). In addition, the amplitude for the same event (time) from other adjacent photo-detectors are compared and centroid determined to find bearing (this in two dimensions, azimuth and elevation).

Figure 8:
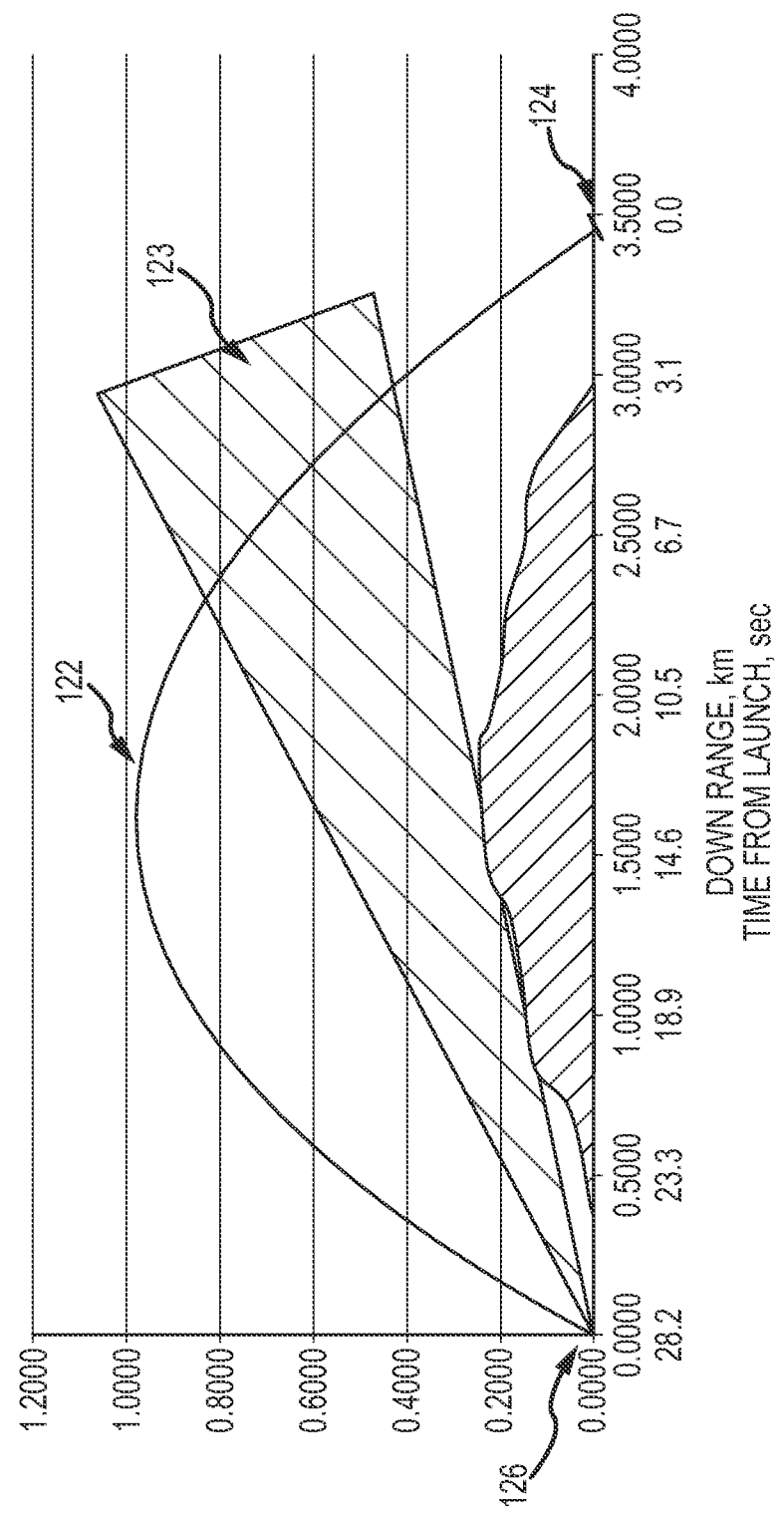
FIG. 8 is an illustration in which rocket classification or identification is used to improve ballistic radar tracking of the rocket.

The rocket launch event and other characteristics may be provided to a radar tracking system 120 to acquire and track the ballistic trajectory 122 of the rocket in a field of view 123 as shown in FIG. 8. During that portion of a rocket trajectory where the target launch and impact points 124 and 126 are not in a radar's field-of-view, the positional data is estimated by extrapolating the estimated equations of motion of the rocket. In the general case neither the firing (launch) point 124 nor the impact point 126 is in the field of view of the radar (and, in any case, there is a need to estimate the coordinates of the point of impact well ahead of the actual impact itself in order to alert ground forces). The accuracy of the extrapolation is a function of several variables, the radar's inherent accuracy, the amount of data collected, the length of extrapolation, the accuracy of the terrain height data at the firing and impact points (or, in the case of direct fire, the time of firing). In addition, the accuracy of the extrapolation is dependent on how accurately the ballistics of the target is modeled. In the case of powered targets, such a rockets, the ballistic models can be quite misleading.

Classification processor 118 processes the sampled data to calculate the periodicity of the variation of the optical radiance of the exhaust plume to estimate the length or speed of sound to length ratio of the rocket motor. The processor uses the rocket motor length or sound ratio to classify or possibly identify the rocket. This information may be passed to the radar tracking system to augment the ballistic model in order to improve the estimates of the impact or firing points.

Classification processor 118 is configured to assemble the sampled data from the plurality of sequences to form a high fidelity time sequence of sampled data for the exhaust plume (step 109). Assuming normalization of the photo detector data, sampled data may be concatenated by selecting the largest amplitude response at each time sample to form the high fidelity sequence. For example, in a 10×10 array, the one photo detector providing the largest amplitude output is selected at each time sample. As the rocket flies through the FOV the photo detector exhibiting the largest amplitude output should track the flight of the rocket. Sampled data may be composited by identifying the photo detector with the largest amplitude response at each time sample, summing the amplitude responses in a given region of interest around that detector and concatenating the summed values. The region of interest could be limited to just the photo detectors immediately adjacent the detector with the maximum amplitude response at a given time sample or could be the entire array or any region in between.

Classification processor 118 is configured to set an event window (step 111) The window may be of a fixed duration to provide a specified spectral resolution or may be of a variable duration in order to capture rocket flight through burn out. The start of the window is suitably registered to the event detection. In other embodiments, launch event processor 116 is configured to execute steps 109 and possibly 111 to assemble and window the sampled data. For example, the high fidelity time sequence may be used to estimate burn time or bearing angle. The window of sampled data is then passed from the launch processor to the classification processor.

Classification processor 118 is configured to process the window of the time sequence of sampled data to generate a signal frequency spectrum (step 113). For example, the processor may compute a Fourier or Cepstral transform to provide the signal frequency spectrum. The signal frequency spectrum will exhibit a mode structure corresponding to the periodicity of the variation of the optical radiance of the exhaust plume.

Classification processor 118 is configured to extract the dominant spectral mode in the signal frequency spectrum (step 115). In an embodiment, the processor thresholds the spectrum and orders the modes by amplitude. The largest amplitude mode being identified as the dominant mode. The processor estimates a length or the speed of sound to length ratio of the rocket motor from the frequency of the dominant mode (step 117). Alternately, the processor could extract the frequencies of adjacent modes and use the difference to estimate the rocket motor length or speed of sound to length ratio.

Classification processor 118 is configured to use the estimated length or speed of sound to length ratio of the rocket motor to select the rocket class or rocket from the library 112 of rocket classes or specific rockets in computer memory 116 (step 119). The processor may be configured to use only the estimated rocket motor length or speed of sound to length ratio to select the rocket class or particular rocket. For example, the processor may be configured to select the rocket class or rocket whose stored length or speed of sound to length ratio is closest to the estimated rocket length or speed of sound to length ratio. Alternately, the processor may be configured to use the rocket motor length or speed of sound to length ratio in combination with other inputs to select the rocket class or particular rocket. The processor may be configured to select the rocket class or rocket based on a metric that combines the various inputs.

The rocket classification or identification may be forwarded to the rocket tracking system. The classification or identification of the rocket can be used, with a database of known rocket characteristics, to determine rocket ballistic characteristics, which in turn can be used by the tracking system to improve the ballistic modeling and thus the accuracy of the estimates of the firing point 124 and impact point 126 as shown in in FIG. 8.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

I claim:

1. A method of classification or identification of a solid propellant rocket, comprising:
   collecting optical radiance in a spectral band over an array of overlapping fields-of-view (FOV) that encompass a flight of a rocket and a rocket exhaust plume;
   detecting the optical radiance from the rocket exhaust plume with an array of one pixel photo detectors sensitive to the spectral band and configured to convert optical radiance to one or more analog electrical signals;
   sampling the one or more analog electrical signals at or above a Nyquist rate of twice the highest measurable frequency component of amplitude modulation of the optical radiance to generate sampled data;
   assembling the sampled data from the one or more electrical signals to form a time sequence of the sampled data for the exhaust plume;
   processing a window of the time sequence of the sampled data to generate a signal frequency spectrum;
   identifying a frequency of a mode in the signal frequency spectrum;
   estimating a length L or speed of sound to length ratio a/L of a rocket motor from the frequency of the mode;
   and using the estimated length L or ratio a/L of the rocket motor to classify or identify the rocket.

2. The method of claim 1, wherein the spectral band comprises one or more bands in visible, IR or UV spectra.

3. The method of claim 1, further comprising providing a library of rocket motors indexed by motor length L or speed of sound to length ratio a/L, and setting the Nyquist rate according to the length of the shortest rocket motor or rocket motor with the highest speed of sound to length ratio.

4. The method of claim 1, wherein the sampling is performed at a rate of at least 5 KHz.

5. The method of claim 1, wherein the window of the time sequence is a fixed duration.

6. The method of claim 1, wherein the window of the time sequence is a duration from rocket launch to rocket motor burn out.

7. The method of claim 1, wherein identifying the frequency comprises identifying a frequency of a dominant mode in the signal frequency spectrum and using the frequency of the dominant mode to estimate the length L or speed of sound to length ratio a/L of the rocket motor.

8. The method of claim 1, further comprising:
   using a radar to track a ballistic trajectory of the rocket in flight to model rocket ballistics to extrapolate forward the ballistic trajectory to estimate a point of rocket impact or to extrapolate backward the ballistic trajectory to estimate a point of rocket launch; and
   using rocket characteristics associated with the rocket classification or identification to augment the model of the rocket ballistics to improve the estimate of the point of rocket impact or the estimate of the point of rocket launch.

9. The method of claim 1, wherein the sampling of the one or more analog electrical signals is synchronized to a reference clock signal to assemble the sampled data from the one pixel detectors to form the time sequence of sampled data.

10. The method of claim 9, wherein the assembling of the sampled data comprises identifying the largest amplitude sample at each sample time and concatenating those largest amplitude samples.

11. The method of claim 9, wherein the assembling of the sampled data comprises identifying a photo detector with the largest sample amplitude at each sample time, summing the sample amplitudes in a region of interest around that photo detector and concatenating the summed values.

12. The method of claim 9, wherein the assembling of the sampled data to form the time sequence of sampled data removes spatial information.

13. The method of claim 1, further comprising:
   processing the sampled data to detect a rocket launch event; and when a rocket launch event is detected, assembling the sampled data associated with the rocket launch event and at least a portion of the initial flight.

14. A method of classification or identification of a solid propellant rocket, comprising:
collecting optical radiance in a spectral band over an array of overlapping fields-of-view (FOV) that encompass a flight of a rocket and a rocket exhaust plume;
detecting the optical radiance from the rocket exhaust plume with an array of one pixel photo detectors sensitive to the spectral band and configured to convert optical radiance to analog electrical signals;
receiving a reference clock signal;
sampling the analog electrical signals at or above a Nyquist rate of twice the highest measurable frequency component of amplitude modulation of the optical radiance to generate a plurality of sequences of sampled data that are synchronized to the external clock signal;
processing the sampled data to detect a rocket launch event;
assembling the sampled data from the plurality of sequences to form a time sequence of the sampled data for the exhaust plume;
processing a window of the time sequence of the sampled data to generate a signal frequency spectrum;
identifying a frequency of a dominant mode in the signal frequency spectrum;
estimating a length L or speed of sound to length ratio a/L of a rocket motor from the frequency of the dominant mode; and
using the estimated length L or ratio a/L of the rocket motor to classify or identify the rocket.

15. A rocket classification unit, comprising:
an optical array configured to collect optical radiance in a spectral band over an array of overlapping fields-of-view (FOV) that encompass a flight of a rocket and a rocket exhaust plume;
an array of one-pixel photo detectors sensitive to the spectral band arranged to detect optical radiance from the overlapping FOV and configured to convert the optical radiance to analog electrical signals;
a reference clock signal;
an array of analog-to-digital converters configured to sample the array of analog electrical signals at or above a Nyquist rate of twice the highest measurable frequency component of amplitude modulation of the optical radiance to generate a plurality of sequences of sampled data that are synchronized to the reference clock signal;
computer memory storing rocket classes or individual rockets indexed by rocket motor length L or speed of sound to length ratio (a/L); and
one or more computer processors configured to
assemble the sampled data from the plurality of sequences to form a time sequence of the sampled data for the exhaust plume;
process a window of the time sequence of the sampled data to generate a signal frequency spectrum;
identify a frequency of a dominant mode in the signal frequency spectrum;
estimate a length L or speed of sound to length ratio a/L of a rocket motor from the frequency of the dominant mode; and
use the estimated length L or ratio a/L of the rocket motor to select the rocket class or rocket from the computer memory.

16. The unit of claim 15, wherein the one or more processors are configured to assemble the sampled data by identifying the largest amplitude sample at each sample time and concatenating those largest amplitude samples.

17. The unit of claim 15, wherein the one or more processors are configured to assemble the sampled data by identifying the photo detector with the largest sample amplitude at each sample time, summing the sample amplitudes in a region of interest around that photo detector and concatenating the summed values.

18. The unit of claim 15, further comprising:
a radar tracker configured to track a ballistic trajectory of the rocket in flight to model rocket ballistics to extrapolate forward the ballistic trajectory to estimate a point of rocket impact or to extrapolate backward the ballistic trajectory to estimate a point of rocket launch,
said radar tracker configured to use rocket characteristics associated with the rocket classification or identification to augment the model of the rocket ballistics to improve the estimate of the point of rocket impact or the estimate of the point of rocket launch.

* * * * *